(12) United States Patent
Kakefuda et al.

(10) Patent No.: US 8,513,422 B2
(45) Date of Patent: Aug. 20, 2013

(54) PIPERIDINE DERIVATIVE

(75) Inventors: Akio Kakefuda, Tokyo (JP); Kazushi Watanabe, Tokyo (JP); Akio Kamikawa, Tokyo (JP); Kentaro Enjo, Tokyo (JP); Takashi Furutani, Tokyo (JP); Minoru Yasuda, Ibaraki (JP)

(73) Assignee: Astellas Pharma Inc., Tokyo (JP)

( * ) Notice: Subject to any disclaimer, the term of this patent is extended or adjusted under 35 U.S.C. 154(b) by 505 days.

(21) Appl. No.: 12/675,744

(22) PCT Filed: Aug. 28, 2008

(86) PCT No.: PCT/JP2008/065429
§ 371 (c)(1),
(2), (4) Date: Feb. 26, 2010

(87) PCT Pub. No.: WO2009/028618
PCT Pub. Date: Mar. 5, 2009

(65) Prior Publication Data
US 2010/0256189 A1 Oct. 7, 2010

(30) Foreign Application Priority Data
Aug. 31, 2007 (JP) ................. 2007-225378

(51) Int. Cl.
A61K 31/445 (2006.01)
C07D 211/32 (2006.01)

(52) U.S. Cl.
USPC .......................... 546/199; 514/323

(58) Field of Classification Search
USPC .......................... 546/198; 514/323
See application file for complete search history.

(56) References Cited

U.S. PATENT DOCUMENTS

| | | | |
|---|---|---|---|
| 6,787,651 B2 | 9/2004 | Stolle et al. | |
| 2005/0250741 A1 | 11/2005 | Lanter et al. | |
| 2005/0282864 A1* | 12/2005 | McArthur et al. | 514/323 |
| 2009/0181960 A1 | 7/2009 | Niimi et al. | |

FOREIGN PATENT DOCUMENTS

| | | |
|---|---|---|
| EP | 0622361 A1 | 11/1994 |
| JP | 6-511238 | 12/1994 |
| JP | 2002-506077 | 2/2002 |
| JP | 2004-529855 | 9/2004 |
| JP | 2005-162657 | 6/2005 |
| RU | 2135478 C1 | 8/1999 |
| WO | WO 93/03012 | 2/1993 |
| WO | WO 98/28292 | 7/1998 |
| WO | WO 99/46279 | 9/1999 |
| WO | WO 02/072548 A2 | 9/2002 |
| WO | WO 03/035621 A1 | 5/2003 |
| WO | WO 03/049736 A1 | 6/2003 |
| WO | WO 2004/064735 A2 | 8/2004 |
| WO | WO 2004/089470 A2 | 10/2004 |
| WO | WO 2005/021531 A1 | 3/2005 |
| WO | WO 2005/040112 A1 | 5/2005 |
| WO | WO 2005/082905 A1 | 9/2005 |
| WO | WO 2005/110985 A2 | 11/2005 |
| WO | WO 2007/030574 A2 | 3/2007 |
| WO | WO 2007/056155 A1 | 5/2007 |
| WO | WO 2007/100066 A1 | 9/2007 |

OTHER PUBLICATIONS

Supplementary European Search Report mailed Aug. 10, 2011 for European Patent Application No. 08 82 8181.
International Search Report from Japanese Patent Office for PCT/JP2008/065429, Dated Nov. 4, 2008.
Lovering, A. L. et al., "Crystal Structures of Prostaglandin D₂ 11-Ketoreductase (AKR1C3) in Complex with the Nonsteroidal Anti-Inflammatory Drugs Flufenamic Acid and Indomethacin," Cancer Research, vol. 64, pp. 1802-1810, (Mar. 1, 2004).
Brozic, P. et al., "Cinnamic Acids as New Inhibitors of 17β-Hydroxysteroid Dehydrogenase Type 5 (AKR1C3)," Molecular and Cellular Endocrinology, vol. 248, pp. 233-235, (2006).
Office Action dated Nov. 11, 2012, for Israeli Patent Application No. 203844.
Office Action dated Mar. 29, 2013 from Japanese Patent Application No. 2009-530181.

* cited by examiner

*Primary Examiner* — Shengjun Wang
(74) *Attorney, Agent, or Firm* — Finnegan, Henderson, Farabow, Garrett & Dunner, L.L.P.

(57) ABSTRACT

As a result of studies on compounds having a selective inhibitory activity against 17βHSD type 5, the present inventors have confirmed that a {1-[(indol-2-yl)carbonyl]piperidyl}alkanol derivative has a potent selective inhibitory activity against 17βHSD type 5. The invention has been completed based on these findings. The compound of the present invention can be used as an agent for treating and/or an agent for preventing diseases associated with 17βHSD type 5, such as benign prostatic hyperplasia and prostate cancer, without accompanying adverse effects due to a decrease in testosterone.

14 Claims, No Drawings

PIPERIDINE DERIVATIVE

TECHNICAL FIELD

The present invention relates to a piperidine compound having a pharmacological activity and/or a salt thereof. Further, the present invention relates to a medicament or a pharmaceutical composition containing the piperidine compound and/or a salt thereof described above as an active ingredient.

BACKGROUND ART

Benign Prostatic Hyperplasia (BPH) is a disease mainly occurring in elder males aged 50 years or above and accompanying urinary disorders, and its incidence rate increases with the age. The number of patients with BPH in Japan has been constantly increasing in recent years with the rapid aging of the population. BPH remarkably deteriorates the quality of life of the aged males due to urinary disorders, and it is an important disease in terms of medical economics since it is the most frequently diagnosed and treated disease in the medical field of urology.

It has been found that two factors, that is, direct urethral compression due to hypertrophy of the prostate (mechanical obstruction) and elevation of intraurethral pressure due to overcontraction of the prostatic smooth muscle via the sympathetic nerve (functional obstruction), are simultaneously involved in urinary disorders accompanying BPH. Drug therapy can deal with both of these mechanisms, and 5α-reductase inhibitors are mainly used for the mechanical obstruction and α1-sympatholytic agents (α1 blockers) are mainly used for the functional obstruction. 5α reductase inhibitors regress the prostate due to their anti-androgenic effect based on the suppression of the conversion of testosterone to 5α-dehydrotestosterone (DHT) which is a more potent androgen produced by a 5α-reductase. Only the prostatic epithelium regresses, however, and it takes a long period of time (several weeks to several months) for the drug efficacy to become apparent. On the other hand, since α1-blockers exert their drug efficacy swiftly after administration and are excellent in safety, α1-blockers are now the first-line agent for treating BPH. However, as a result of the long-term clinical studies, since a 5α-reductase inhibitor significantly delayed the transfer to invasive therapy as compared with the single use of an α1-blocker, and the like ("The New England Journal of Medicine", 2003, Vol. 349, p. 2387-2398), the usefulness of 5α-reductase inhibitors has recently been recognized again.

It has been considered that DHT in the prostate is produced by 5α-reductase from testosterone, which is produced in the testes and secreted endocrinologically to the prostate. It has been reported recently, however, that about half of DHT and its precursor, testosterone, in prostate, are synthesized from dehydroepiandrosterone (DHEA), a steroid derived from an adrenal, in cells of the prostate ("Frontier in Neuroendocrinology", 2001, Vol. 22, p. 185-212). This kind of sex hormone production system in the cells of the sex hormone target organs is called intracrinology.

It is difficult for 5α-reductase inhibitors to inhibit the local testosterone synthesis (intracrine testosterone synthesis) in the prostate. For example, it has been reported that the concentration of DHT in the prostate of the patients with BPH was decreased after the administration of finasteride, a 5α-reductase inhibitor, to about 20% of the concentration before the administration, while the concentration of testosterone, a precursor, in the prostate was inversely increased 4-fold ("The Journal of Urology", 1999, Vol. 161, p. 332-337). It means that although the 5α-reductase inhibitor has an effect of reducing DHT concentration in the prostate, it has no effect of reducing the concentration of testosterone in the prostate and instead elevates the concentration. Since testosterone has an androgen receptor binding activity of about the half of that of DHT, this local elevation of the concentrations of testosterone in the prostate is considered to be partly responsible for insufficient drug efficacy of finasteride for BPH.

Anti-androgen therapies using surgical castration and gonadotropin releasing hormone agonists are also used for prostate cancer. These anti-androgen therapies have been reported to exert an insufficient effect of reducing the concentrations of testosterone in the prostate. For example, in patients with prostate cancer who receive the anti-androgen therapy, the concentration of testosterone in the blood decreased to about 10% of the concentration before the therapy, while the concentration of DHT in the prostate remained at about 50% ("The Journal of Clinical Endocrinology and Metabolism", 1995, Vol. 80, p. 1066-1071). It suggests that the concentration of testosterone in the prostate is also not sufficiently reduced. Further, androgen receptors were localized in nuclei also in a prostate cancer recurring after anti-androgen therapy (Hormone Refractory Prostate Cancer), and no significant difference was observed between the concentration of testosterone in recurrent prostate cancer tissues and that in the normal prostate ("Clinical Cancer Research", 2004, Vol. 10, p. 440-448). These reports strongly suggest that the effect of reducing the concentrations of testosterone in the prostate in existing therapeutic methods is quite insufficient for treating recurrent prostate cancer and that suppression of the testosterone synthesizing mechanism in the prostate, that is, intracrine testosterone synthesis in the prostate may be a new target of prostate cancer therapy.

Based on the known arts described above, since inhibitors of intracrine testosterone synthesis in the prostate have an effect of reducing the concentrations of testosterone in the prostate and no effect of reducing the concentrations of testosterone in the blood, the inhibitors are expected to be very attractive agent for treating BPH and/or an agent for treating prostate cancer, (1) which can reduce not only the concentration of testosterone but also the concentration of DHT in the prostate and (2) which can avoid the adverse effects due to the suppression of the concentration of the testosterone derived from testes in the blood.

17β-hydroxysteroid dehydrogenase (17βHSD) is essential for the biosynthesis of testosterone. There are several subtypes of 17βHSD. 17βHSD type 5 is highly expressed in a human prostate and increases of the expression were reported for prostate cancer and recurrent prostate cancer ("Steroids", 2004, Vol. 69, p. 795-801; and "Cancer Research", 2006, Vol. 66, p. 2815-2825). On the other hand, almost all the testosterone in the blood is produced by 17βHSD type 3 in testes and the expression of 17βHSD type 3 is rarely observed in other tissues including the prostate ("Nature Genetics", 1994, Vol. 7, p. 34-39). 17βHSD type 5 is thus considered to be responsible for the intracrine testosterone synthesis in the prostate and selective inhibitors of 17βHSD type 5 are expected to suppress intracrine testosterone synthesis in the prostate selectively. Further, since the contribution of 17βHSD type 5 has been pointed out also in estrogen-dependent tissues such as the mammary gland and the like, the selective inhibitors are expected to be effective for estrogen-dependent diseases such as breast cancer and the like ("Endocrine Reviews", 2003, Vol. 24, p. 152-182). In addition, it is reported that AKR1C3 (another name for 17βHSD type 5), which is a subtype of aldo-keto reductase (AKR), metabolizes Polycyclic Aromatic Hydrocarbon (PAH) to generate reactive oxygen species (ROS) ("The Journal of Biological Chemistry", 2002, Vol. 277, No. 27, p. 24799-24808) and that single nucleotide polymorphism (SNP) of AKR1C3 gene relating to oxidative stress correlates with a risk of lung cancer ("Carcinogenesis", 2004, Vol. 25, No. 11, p. 2177-2181). That is, it is suggested that the activity of AKR1C3 in the lungs increases the risk of lung cancer via generation of ROS from PAH and selective inhibitors of 17βHSD type 5 are expected to be effective for lung cancer.

As 17βHSD type 5 inhibitors, steroid derivatives (Patent Document 1) and NSAIDs (Non-steroidal Anti-Inflammatory Drugs) such as flufenamic acid, indomethacin and the like (Non-Patent Document 1), cinnamic acid derivatives (Non-Patent Document 2) and the like have been reported. Although the mechanism of action is different, an indazole derivative containing a compound of formula (A) is known to be effective for BPH (Patent Document 2).

[Chem. 1]

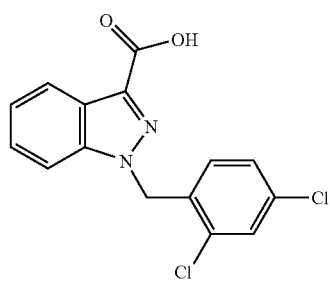

(A)

Patent Document 3 discloses that N-substituted benzimidazole derivatives including a compound of formula (B) have an inhibitory action against the c-Kit oncogene and are useful for prostate cancer or the like. However, there is no disclosure of an indolyl group, and there is also no description of an inhibitory action against 17βHSD type 5.

[Chem. 2]

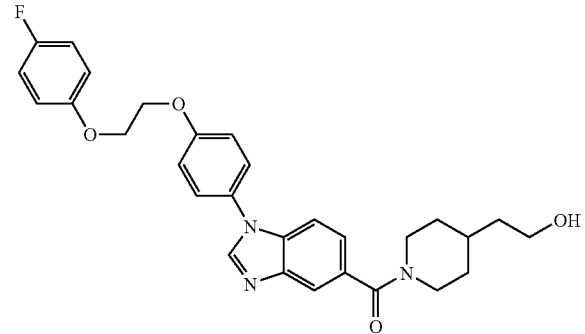

(B)

Patent Document 4 discloses that benzimidazole derivatives including a compound of formula (C) have a tyrosine kinase regulatory action and are useful for prostate cancer or the like. However, there is no disclosure of an indolyl group, and there is also no description of an inhibitory action against 17βHSD type 5.

[Chem. 3]

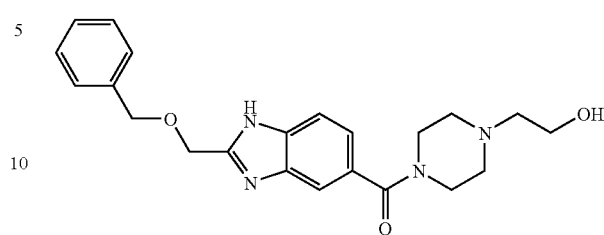

(C)

Patent Document 5 discloses that indole derivatives including a compound of formula (D) have a histamine H4 antagonistic action, and are useful for inflammation. However, there is no disclosure of a non-basic (piperidyl) alkanol structure, and there is also no description of an inhibitory action against 17βHSD type 5, and effectiveness for BPH, prostate cancer and the like.

[Chem. 4]

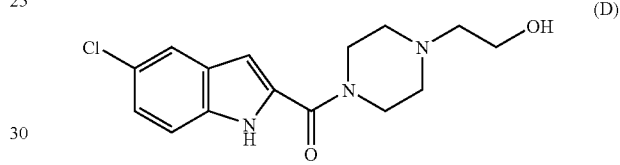

(D)

Patent Document 6 discloses that indole derivatives including a compound of formula (E) have a cannabinoid receptor regulatory action, and are useful for cerebrovascular disorders and the like. However, there is also no description of an inhibitory action against 17βHSD type 5, and effectiveness for BPH, prostate cancer and the like.

[Chem. 5]

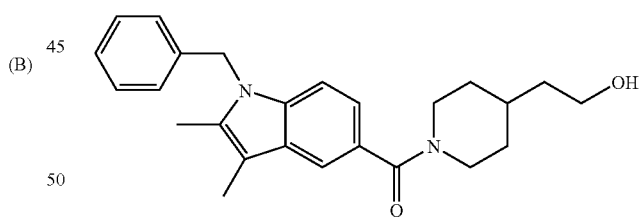

(E)

[Patent Document 1] Pamphlet of International Publication No. WO99/046279

[Patent Document 2] Pamphlet of International Publication No. WO2004/064735

[Patent Document 3] Pamphlet of International Publication No. WO2005/021531

[Patent Document 4] Pamphlet of International Publication No. WO2007/056155

[Patent Document 5] Pamphlet of International Publication No. WO2002/072548

[Patent Document 6] JP-A-2005-162657

[Non-Patent Document 1] Cancer Research, 2004, Vol. 64, p. 1802-1810

[Non-Patent Document 2] Molecular and Cellular Endocrinology, 2006, Vol. 248, p. 233-235

DISCLOSURE OF THE INVENTION

Problem that the Invention is to Solve

An object of the present invention is to provide a compound useful as a medicament having a selective inhibitory activity against 17βHSD type 5, in particular as an agent for treating benign prostatic hyperplasia and/or prostate cancer.

Means for Solving the Problem

As a result of intensive studies on compounds having a selective inhibitory activity against 17βHSD type 5, the present inventors have found that a {1-[(indol-2-yl)carbonyl]piperidyl}alkanol derivative has a potent selective inhibitory activity against 17βHSD type 5 and can be an agent for treating and/or an agent for preventing a disease associated with 17βHSD type 5, such as benign prostatic hyperplasia and prostate cancer, without accompanying adverse effects due to a decrease in testosterone. The invention has been completed based on these findings.

That is, the present invention relates to a compound of formula (I) or a salt thereof, and a pharmaceutical composition comprising the compound of formula (I) or a salt thereof and an excipient.

[Chem. 6]

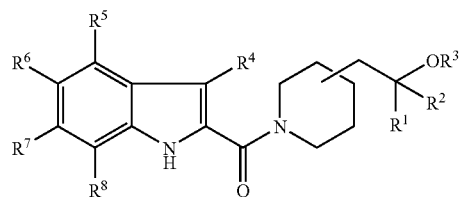

in formula (I), $R^1$, $R^2$, and $R^3$, which are the same or different from each other, are H or lower alkyl;

$R^4$, $R^5$, $R^6$, $R^7$, and $R^8$, which are the same or different from each other, are H, lower alkyl, halogen, halogeno lower alkyl, nitro, —X-cycloalkyl which may be substituted, —X-aryl which may be substituted, —X-heterocyclic group which may be substituted, —X—COOR$^0$, —X—CONR$^{10}$R$^{11}$, —X—CN, —X—SR$^0$, —X—S(O)-lower alkyl, —X—S(O)$_2$-lower alkyl, —X—NR$^{10}$R$^{11}$, —X—NR$^0$C(O)R$^{10}$, —X—NR$^0$C(O)OR$^{10}$, —X—NR$^0$C(O)NR$^{10}$R$^{11}$, —X—NR$^0$S(O)$_2$R$^{10}$, —X—O-halogeno lower alkyl, —X—O—X-cycloalkyl which may be substituted, —X—O—X-aryl which may be substituted, —X—O—X-heterocyclic group which may be substituted, or —X—O-lower alkylene-OR$^0$; or $R^6$ and $R^7$ are combined to form —O-lower alkylene-O—;

$R^0$, which is the same or different from each other, is H or lower alkyl;

$R^{10}$ and $R^{11}$, which are the same or different from each other, are H, lower alkyl, halogeno lower alkyl, —X-cycloalkyl, —X-aryl, or —X-heterocyclic group; or $R^{10}$ and $R^{11}$, together with N to which they are bonded, form a saturated heterocyclic group which may be substituted; and X, which is the same or different from each other, is a bond or lower alkylene.

In the present specification, the symbols defined above are used to represent the same meanings unless otherwise particularly noted.

Further, the present invention relates to a pharmaceutical composition for treating and/or preventing a disease associated with 17βHSD type 5, comprising the compound of formula (I) or a salt thereof, namely, an agent for preventing and/or an agent for treating a disease associated with 17βHSD type 5, comprising the compound of formula (I) or a salt thereof.

Further, the present invention relates to use of the compound of formula (I) or a salt thereof, for the manufacture of a pharmaceutical composition for treating and/or preventing a disease associated with 17βHSD type 5

Further, the present invention relates to a method for treating and/or preventing a disease associated with 17βHSD type 5, comprising administering an effective amount of the compound of formula (I) or a salt thereof to a patient Further, the present invention relates to an inhibitor of 17βHSD type 5, comprising the compound of formula (I) or a salt thereof.

Further, the present invention relates to a method for producing a pharmaceutical composition for preventing or treating a disease associated with 17βHSD type 5, comprising mixing the compound of formula (I) or a salt thereof, and a pharmaceutically acceptable carrier, solvent, or excipient.

Further, the present invention relates to a commercial package, comprising a pharmaceutical composition containing the compound of formula (I) or a salt thereof; and a description that the compound of formula (I) or a salt thereof is capable of being used or should be used for treating and/or preventing a disease associated with 17βHSD type 5.

Effect of the Invention

The compound of formula (I) inhibits 17βHSD type 5 selectively. Accordingly, the compound of formula (I) can be used as an agent for preventing and/or treating a disease associated with 17βHSD type 5. For example, it can be used as an agent for preventing and/or treating a disease associated with androgen, as the androgen synthesis is suppressed by the inhibition of 17βHSD type 5.

BEST MODE FOR CARRYING OUT THE INVENTION

Hereinafter, the present invention will be described in more detail.

In the definitions of the present specification, the "alkyl" and "alkylene" mean a linear or branched hydrocarbon chain unless otherwise particularly noted.

The "lower alkyl" means alkyl having 1 to 6 carbon atoms (hereinafter, referred to as "$C_{1-6}$"), and examples thereof include methyl, ethyl, n-propyl, isopropyl, n-butyl, isobutyl, sec-butyl, tert-butyl, n-pentyl, n-hexyl group, and the like. In another embodiment, it is $C_{1-4}$ alkyl. In yet another embodiment, it is methyl, ethyl, n-propyl, isopropyl, or tert-butyl.

The "lower alkylene" means $C_{1-6}$ alkylene, and examples thereof include methylene, ethylene, trimethylene, tetramethylene, pentamethylene, hexamethylene, propylene, methylmethylene, ethylethylene, 1,2-dimethylethylene, 1,1,2,2-tetramethylethylene group, and the like. In another embodiment, it is $C_{1-5}$ alkylene. In yet another embodiment, it is methylene, ethylene, trimethylene, tetramethylene, or pentamethylene.

The "halogen" means F, Cl, Br, or I.

The "halogen lower alkyl" is lower alkyl substituted with one or more halogens. In another embodiment, it is lower alkyl substituted with 1 to 5 halogens. In yet another embodiment, it is trifluoromethyl.

The "cycloalkyl" is a $C_{3-10}$ saturated hydrocarbon ring group which may be bridged. Examples thereof include cyclopropyl, cyclobutyl, cyclopentyl, cyclohexyl, cycloheptyl, cyclooctyl, bicyclo[2.2.1]heptyl, adamantyl group and the like. In another embodiment, it is $C_{3-8}$ cycloalkyl. In yet another embodiment, it is cyclopropyl, cyclobutyl, cyclopentyl, or cyclohexyl.

The "aryl" is a $C_{6-14}$ monocyclic to tricyclic aromatic hydrocarbon ring group which contains a ring group condensed with $C_{5-8}$ cycloalkene at the double bond site thereof. Examples thereof include phenyl, naphthyl, tetrahydronaphthalenyl, indenyl, fluorenyl group, and the like. In another embodiment, it is phenyl, or naphthyl. In yet another embodiment, it is phenyl.

The "heterocyclic" group means a ring group selected from i) a monocyclic 3- to 8-membered, and in another embodiment, 5- to 7-membered monocyclic heterocycle, containing 1 to 4 hetero atoms selected from O, S and N, and ii) a bicyclic to tricyclic heterocycle containing 1 to 5 hetero atoms selected from O, S and N, which is formed by ring condensation of the monocyclic heterocycle with one or two rings selected from the group consisting of a monocyclic heterocycle, a benzene ring, $C_{5-8}$ cycloalkane, and $C_{5-8}$ cycloalkene. The ring atom, S or N, may be oxidized to form an oxide or a dioxide. Further, it may be bridged or form a spiro ring.

Examples of the "heterocyclic" group includes aziridinyl, azetidyl, pyrrolidinyl, piperidyl, azepanyl, piperazinyl, homopiperazinyl, oxiranyl, oxetanyl, tetrahydrofuranyl, tetrahydropyranyl, tetrahydrothiopyranyl, morpholinyl, homomorpholinyl, thiomorpholinyl, pyrrolyl, indolyl, imidazolyl, pyrazolyl, pyridyl, pyrimidinyl, pyrazinyl, triazolyl, tetrazolyl, furyl, thienyl, oxazolyl, isooxazolyl, oxadiazolyl, thiazolyl, thiadiazolyl, benzimidazolyl, quinolyl, quinazolyl, quinoxalinyl, benzofuranyl, benzothiophenyl, benzoxazolyl, benzthiazolyl, carbazolyl, indolinyl, tetrahydroquinolinyl, tetrahydroisoquinolinyl, quinuclidinyl, dibenzofuranyl, dibenzofuranyl group, and the like.

In another embodiment, it is a monocyclic or bicyclic 5- to 10-membered heterocyclic group.

In yet another embodiment, it is pyrrolidinyl, piperidyl, azepanyl, piperazinyl, homopiperazinyl, oxiranyl, oxetanyl, tetrahydrofuranyl, tetrahydropyranyl, tetrahydrothiopyranyl, morpholinyl, homomorpholinyl, thiomorpholinyl, indolyl, imidazolyl, pyridyl, pyrimidinyl, pyrazinyl, triazolyl, tetrazolyl, furyl, thienyl, oxazolyl, isooxazolyl, thiadiazolyl, benzimidazolyl, tetrahydroquinolinyl, tetrahydroisoquinolinyl, or dibenzofuranyl.

The "saturated heterocyclic" group means, among the above "heterocyclic" group, a group in which ring-forming bonds are all single bonds.

Examples of the "saturated heterocyclic" group include pyrrolidinyl, piperidyl, azepanyl, piperazinyl, homopiperazinyl, oxiranyl, oxetanyl, tetrahydrofuranyl, tetrahydropyranyl, tetrahydrothiopyranyl, morpholinyl, homomorpholinyl, thiomorpholinyl group, and the like.

The "which may be substituted" in the present specification means unsubstituted or substituted with 1 to 5 substituents. Further, if there are multiple substituents, the substituents may be the same or different from each other.

The substituents for the "cycloalkyl which may be substituted", "aryl which may be substituted" or "heterocyclic group which may be substituted" in $R^4$, $R^5$, $R^6$, $R^7$ and $R^8$ include, for example, lower alkyl, halogen, halogeno lower alkyl, nitro, —X—CN, —X—OR$^0$, —X—SR$^0$, —X—S(O)-lower alkyl, —X—S(O)$_2$-lower alkyl, —X—NR$^{10}$R$^{11}$, —X—NR$^0$C(O)R$^{10}$, —X—NR$^0$C(O)OR$^{10}$, —X—NR$^0$C(O)NR$^{10}$R$^{11}$, —X—NR$^0$S(O)$_2$R$^{10}$, —X—O-halogeno lower alkyl, or —X—O-lower alkylene-OR$^0$. In another embodiment, examples thereof include groups selected from lower alkyl, halogen, halogeno lower alkyl, —CN, and OR$^0$. In yet another embodiment, examples thereof include groups selected from methyl, ethyl, F, Cl, trifluoromethyl, and methoxy.

Although the "cycloalkyl", "phenyl", "cyclohexyl" and the like are described as monovalent groups in the present specification for convenience, they may be multivalent groups of divalent or higher valency according to their structures. The present invention encompasses these structures. Specific embodiments of the divalent groups correspond to those having the suffixes of the above ring groups converted into diyl in accordance with the Nomenclature of Organic Chemistry. For example, a divalent group corresponding to a phenyl group that is a monovalent group is phenylene.

The "selective inhibitor of 17βHSD type 5" means an inhibitor in which an inhibitory activity against 17βHSD type 3 exhibits 3-fold or more, preferably 10-fold or more, and more preferably 100-fold or more value relative to an inhibitory activity against human 17βHSD type 5 (AKR1C3), in terms of IC$_{50}$ value.

An embodiment of the compound of formula (I) of the present invention will be described below.

(1) A compound of formula (Ia).

[Chem. 7]

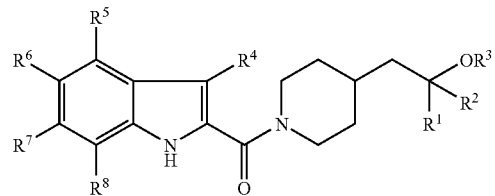

(Ia)

(2) The compound wherein $R^1$ is H.
(3) The compound wherein $R^1$ is lower alkyl.
(4) The compound wherein $R^1$ is methyl.
(5) The compound wherein $R^2$ is H.
(6) The compound wherein $R^2$ is lower alkyl.
(7) The compound wherein $R^2$ is methyl.
(8) The compound wherein $R^3$ is H.
(9) The compound wherein $R^3$ is lower alkyl.
(10) The compound wherein $R^4$ is H, lower alkyl, halogen, or —O-lower alkyl.
(11) The compound wherein $R^4$ is H.
(12) The compound wherein $R^4$ is lower alkyl.
(13) The compound wherein $R^4$ is halogen.
(14) The compound wherein $R^4$ is —O-lower alkyl.
(15) The compound wherein $R^5$ is H, lower alkyl, halogen, or —O-lower alkyl.
(16) The compound wherein $R^5$ is H.
(17) The compound wherein $R^5$ is lower alkyl.
(18) The compound wherein $R^5$ is halogen.
(19) The compound wherein $R^5$ is —O-lower alkyl.
(20) The compound wherein $R^6$ is H, lower alkyl, halogen, halogeno lower alkyl, nitro, cycloalkyl, OH, or —O-lower alkyl.
(21) The compound wherein $R^6$ is lower alkyl, halogen, or —O-lower alkyl.

(22) The compound wherein $R^6$ is H.
(23) The compound wherein $R^6$ is lower alkyl.
(24) The compound wherein $R^6$ is halogen.
(25) The compound wherein $R^6$ is halogeno lower alkyl.
(26) The compound wherein $R^6$ is nitro.
(27) The compound wherein $R^6$ is cycloalkyl.
(28) The compound wherein $R^6$ is OH.
(29) The compound wherein $R^6$ is —O-lower alkyl.
(30) The compound wherein $R^7$ is H, lower alkyl, halogen, or —O-lower alkyl.
(31) The compound wherein $R^7$ is H.
(32) The compound wherein $R^7$ is lower alkyl.
(33) The compound wherein $R^7$ is halogen.
(34) The compound wherein $R^7$ is —O-lower alkyl.
(35) The compound wherein $R^8$ is H, lower alkyl, halogen, or —O-lower alkyl.
(36) The compound wherein $R^8$ is H.
(37) The compound wherein $R^8$ is lower alkyl.
(38) The compound wherein $R^8$ is halogen.
(39) The compound wherein $R^8$ is —O-lower alkyl.
(40) The compound which is a combination of any two or more of the groups described in the above (1) to (39).

Specific examples of the compound of the above (40) include the following compounds.

(41) The compound described in (1), wherein $R^1$ and $R^3$ are H.
(42) The compound described in (41), wherein $R^4$, $R^5$, $R^7$, and $R^8$, which are the same or different from each other, are H, lower alkyl, halogen, or —O-lower alkyl, $R^6$ is H, lower alkyl, halogen, halogeno lower alkyl, nitro, cycloalkyl, OH, or —O-lower alkyl.
(43) The compound described in (1), wherein $R^1$ and $R^2$ are lower alkyl, and $R^3$ is H.
(44) The compound described in (43), wherein $R^4$, $R^5$, $R^7$, and $R^8$, which are the same or different from each other, are H, lower alkyl, halogen, or —O-lower alkyl.
(45) The compound described in (43) or (44), wherein $R^6$ is H, lower alkyl, halogen, halogeno lower alkyl, nitro, cycloalkyl, OH, or —O-lower alkyl.
(46) The compound described in (43) to (45), wherein $R^6$ is lower alkyl, halogen, or —O-lower alkyl.

Another embodiment of the compound of formula (I) of the present invention will be described below.

(47) The compound described in (1), wherein $R^1$, $R^2$, $R^3$, and $R^4$, which are the same or different from each other, are H or lower alkyl, $R^5$ is H, lower alkyl, halogen, or —O-lower alkyl, $R^6$ is H, lower alkyl, halogen, OH, —O-lower alkyl, —O-lower alkylene-phenyl, —O-halogeno lower alkyl, nitro, amino, -amino-C(O)-lower alkyl, or pyrrolyl, $R^7$ is H, halogen, OH, or —O-lower alkyl, or $R^6$ and $R^7$ are combined to form —O-lower alkylene-O—, and $R^8$ is H or halogen.
(48) The compound described in (47), wherein $R^1$ is lower alkyl.
(49) The compound described in (48), wherein $R^1$ is methyl.
(50) The compound described in (47), wherein $R^2$ is lower alkyl.
(51) The compound described in (50), wherein $R^2$ is methyl.
(52) The compound described in (47), wherein $R^3$ is H.
(53) The compound described in (47), wherein $R^4$ is H.
(54) The compound described in (47), wherein $R^5$ is H, Cl, or methyl.
(55) The compound described in (47), wherein $R^6$ is H, Cl, methyl, methoxy, or nitro.
(56) The compound described in (47), wherein $R^7$ is H.
(57) The compound described in (47), wherein $R^8$ is H or Cl.
(58) The compound which is a combination of any two or more of the groups described in the above (48) to (57).

Specific compounds encompassed by the present invention include the following compounds.

2-{1-[(5-methyl-1H-indol-2-yl)carbonyl]piperidin-4-yl}ethanol,
1-[1-(1H-indol-2-ylcarbonyl)piperidin-4-yl]propan-2-ol,
1-[1-(1H-indol-2-ylcarbonyl)piperidin-4-yl]-2-methylpropan-2-ol,
2-methyl-1-{1-[(4-methyl-1H-indol-2-yl)carbonyl]piperidin-4-yl}propan-2-ol,
2-methyl-1-{1-[(5-methyl-1H-indol-2-yl)carbonyl]piperidin-4-yl}propan-2-ol,
1-{1-[(3,5-dimethyl-1H-indol-2-yl)carbonyl]piperidin-4-yl}-2-methylpropan-2-ol,
1-{1-[(5-tert-butyl-1H-indol-2-yl)carbonyl]piperidin-4-yl}-2-methylpropan-2-ol,
1-{1-[(4-fluoro-1H-indol-2-yl)carbonyl]piperidin-4-yl}-2-methylpropan-2-ol,
1-{1-[(5-fluoro-1H-indol-2-yl)carbonyl]piperidin-4-yl}-2-methylpropan-2-ol,
1-{1-[(4-chloro-1H-indol-2-yl)carbonyl]piperidin-4-yl}-2-methylpropan-2-ol,
1-{1-[(5-chloro-1H-indol-2-yl)carbonyl]piperidin-4-yl}-2-methylpropan-2-ol,
1-{1-[(5-bromo-1H-indol-2-yl)carbonyl]piperidin-4-yl}-2-methylpropan-2-ol,
1-{1-[(7-chloro-5-fluoro-1H-indol-2-yl)carbonyl]piperidin-4-yl}-2-methylpropan-2-ol,
2-{[4-(2-hydroxy-2-methylpropyl)piperidin-1-yl]carbonyl}-1H-indol-5-ol,
1-{1-[(4-methoxy-1H-indol-2-yl)carbonyl]piperidin-4-yl}-2-methylpropan-2-ol,
1-{1-[(5-methoxy-1H-indol-2-yl)carbonyl]piperidin-4-yl}-2-methylpropan-2-ol,
1-{1-[(6-methoxy-1H-indol-2-yl)carbonyl]piperidin-4-yl}-2-methylpropan-2-ol,
2-methyl-1-(1-{[5-(trifluoromethoxy)-1H-indol-2-yl]carbonyl}piperidin-4-yl)propan-2-ol, and
2-methyl-1-{1-[(5-nitro-1H-indol-2-yl)carbonyl]piperidin-4-yl}propan-2-ol.

The compound of formula (I) may in some cases exist in the form of tautomers or geometrical isomers, depending on the kind of substituents. In the present specification, the compound of formula (I) may be described only in one form of the isomers, but the present invention includes other isomers as well as isolated forms or mixtures thereof.

Further, the compound of formula (I) may have asymmetric carbon atoms or axial asymmetries in some cases, and correspondingly, it may exist in the form of optical isomers. The present invention also includes isolates or mixtures of optical isomers of the compound of formula (I).

Further, the present invention includes a pharmaceutically acceptable prodrug of the compound of formula (I). The pharmaceutically acceptable prodrug is a compound having a group which can be converted into an amino group, a hydroxyl group, a carboxyl group or the like by solvolysis or under a physiological condition. Examples of the group which forms a prodrug include the groups as described, for example, in Prog. Med., 5, 2157-2161 (1985) or "Pharmaceutical Research and Development" (Hirokawa Publishing Company, 1990), Vol. 7, "Drug Design", pp. 163-198.

In addition, the salt of the compound of formula (I) is a pharmaceutically acceptable salt of the compound of formula (I), and may form an acid addition salt or salt with a base, depending on the kind of substituents. Specifically, examples thereof include acid addition salts with inorganic acids such as hydrochloric acid, hydrobromic acid, hydroiodic acid, sulfuric acid, nitric acid, and phosphoric acid, or with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methanesulfonic acid, ethanesulfonic acid, benzenesulfonic acid, p-toluenesulfonic acid, aspartic acid, and glutamic acid, salts with inorganic bases such as sodium, potassium, magnesium, calcium, and aluminum, or with organic bases such as methylamine, ethylamine, ethanolamine, lysine, and ornithine, salts with various amino acids and amino acid derivatives such as acetylleucine, ammonium salts, and the like.

Further, the present invention also includes various hydrates or solvates, and polymorphic crystal substances of the compound of formula (I) and a salt thereof. Further, the present invention also includes compounds labeled with various radioactive or non-radioactive isotopes.

(Production Processes)

The compound of formula (I) and a salt thereof can be produced by utilizing the characteristics based on the types of its basic skeleton or substituents and by applying various known synthetic methods. At this time, it is in some cases effective, in terms of production techniques, that the functional group is replaced with an appropriate protecting group (a group that can be easily converted into the functional group) in the stage of a starting material to intermediate depending on the type of the functional group during the production. Examples of such functional groups include an amino group, a hydroxyl group, a carboxyl group, and the like, and examples of such protecting groups include protecting groups described for example in "Protective Groups in Organic Synthesis (the third edition, 1999)" edited by Greene and Wuts, or the like, which may be appropriately selected and used depending on the reaction conditions. In these methods, a desired compound can be obtained by introducing the protecting group and carrying out the reaction, and then removing the protecting group, if desired.

In addition, the prodrug of the compound of formula (I) can be produced in the same manner as the case of the protecting groups, by carrying out the reaction after introducing a specific group at the stage of starting materials to intermediates or using the compound of formula (I) obtained. The reaction can be carried out by applying methods known to those skilled in the art, such as the usual esterification, amidation, dehydration and the like.

Hereinafter, the representative production processes for the compound of formula (I) will be described. Each of the production processes may also be carried out with reference to References appended to the present description. Further, the production processes of the present invention are not limited to the examples as shown below.

[Chem. 8]

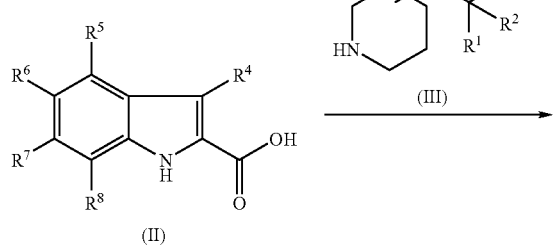

(II)

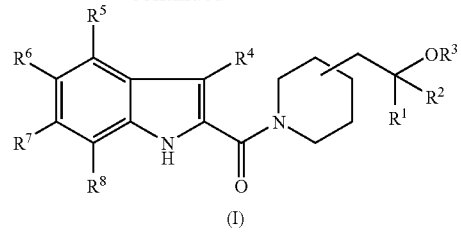

(I)

The compound of formula (I) can be produced by reacting a compound (II) with a compound (III).

The reaction can be carried out using the compound (II) and the compound (III) in equivalent amounts or either thereof in an excessive amount in the presence of a condensing agent, from under cooling to under heating, preferably at −20° C. to 60° C. usually stirring for 0.1 hour to 5 days, in a solvent which is inert to the reaction.

Here, the solvent is not particularly limited, but examples thereof include aromatic hydrocarbons such as benzene, toluene, and xylene; halogenated hydrocarbons such as dichloromethane, 1,2-dichloroethane, and chloroform; ethers such as diethyl ether, tetrahydrofuran, dioxane, and dimethoxyethane; N,N-dimethylformamide, dimethylsulfoxide, ethyl acetate, acetonitrile, water or a mixture thereof.

Examples of the condensing agent include 1-ethyl-3-(3-dimethylaminopropyl)carbodiimide or a hydrochloride thereof, dicyclohexylcarbodiimide, 1,1'-carbonyldiimidazole, diphenylphosphoryl azide, phosphorus oxychloride and the like, but are not limited to these. It may be advantageous in some cases for the reaction to use, for example, an additive (for example, 1-hydroxybenzotriazole or the like). It may be advantageous in some cases for the smooth progress of the reaction to carry out the reaction in the presence of an organic base such as triethylamine, N,N-diisopropylethylamine, or N-methylmorpholine, or an inorganic base such as potassium carbonate, sodium carbonate, or potassium hydroxide.

Further, a method can also be used in which the carboxylic acid compound (II) is converted into a reactive derivative thereof, and then reacted with the compound (III). Examples of the reactive derivative of the carboxylic acid include an acid halide obtained by the reaction with a halogenating agent such as phosphorus oxychloride or thionyl chloride, a mixed acid anhydride obtained by the reaction with isobutyl chloroformate or the like, and an active ester obtained by the condensation with 1-hydroxybenzotriazole or the like. The reaction between these reactive derivatives and the compound (III) can be carried out from under cooling to under heating, preferably at −20° C. to 60° C., in a solvent which is inert to the reaction such as halogenated hydrocarbons, aromatic hydrocarbons, or ethers.

Further, various substituents on groups $R^1$ to $R^8$ in the compound of formula (I) can be easily converted into other functional groups by using the compound of formula (I) as a starting material and applying reactions described in the following Examples, reactions apparent to those skilled in the art, or modified methods thereof. For example, such reactions can be carried out by any combination of processes that can be conventionally employed by those skilled in the art, for example O-alkylation, N-alkylation, reduction, hydrolysis, amidation, and the like. Examples thereof will be described below.

The compound of formula (I) having an amino group can be produced by the reduction of a nitro group, for example, with reference to the method described in "The fourth edition of Courses in Experimental Chemistry (Vol. 26)", edited by The Chemical Society of Japan, Maruzen, 1992.

The compound of formula (I) having an amide group can be produced by the acylation of an amino group, for example, with reference to the methods described in "The fourth edition of Courses in Experimental Chemistry (Vol. 22)", edited by The Chemical Society of Japan, Maruzen, 1992 and "The fifth edition of Courses in Experimental Chemistry (Vol. 16)", edited by The Chemical Society of Japan, Maruzen, 2005; or "Compendium of Organic Synthetic Methods", Vols. 1 to 3.

The compound of formula (I) having an o-dihydroxyphenyl group can be produced by the cleavage of a 1,3-dioxolane ring, for example, with reference to the method described in "Journal of Medicinal Chemistry", 2001, 44, 1794-1801.

The compound of formula (I) having a phenyl group substituted with pyrrolyl group can be produced by the reaction to form a pyrrole ring, for example, with reference to the method described in "Tetrahedron Letters" 1993, 34, 1929-1930.

(Production of Starting Compound)

The starting compound (II) can be produced by the indole synthesis reaction of Fischer, for example, with reference to the method described in "The Fischer Indole Synthesis" edited by Robinson, 1982. The starting compound (III) having a tertiary alcohol can be produced by the reaction of a carboxylic acid derivative (such as ester) with a Grignard reagent, for example, with reference to the method described in "Synthesis" 1983, 12, 1030-1031.

(Pharmacological Test)

An excellent selective inhibitory activity against human 17βHSD type 5 of the compounds of the present invention was confirmed by test methods described in sections 1 to 3 below. The test may be carried out by referring to the details of test procedure described in Maniatis, T. et al., Molecular Cloning—A Laboratory Manual Cold Spring Harbor Laboratory, NY (1982), and the like. In addition, genes encoding human 17βHSD type 5 and type 3 described in sections 1 and 2 below, and human 17βHSD type 5 and type 3 can be obtained by the method described in Molecular Endocrinology, 1997, 11(13), 1971-1984.

1. Isolation of Gene Encoding Human 17βHSD Type 5 and Enzyme Purification

A full-length cDNA encoding human 17βHSD type 5 used in the pharmacological test of the present invention was obtained by the PCR method using a cDNA derived from a human lung cancer-derived cell line, A549 cells as a template. The nucleotide sequence of the obtained cDNA was analyzed by the dideoxyterminator method, and the clone matched with the known human 17βHSD type 5 sequence (GenBank accession No. NM_003739) was selected. *Escherichia coli* BL21 was transformed with a plasmid containing the cDNA and cultured on a large scale. The proteins were purified by using GSTrapFF column (manufactured by Amersham) and PreScissionProtease (manufactured by Amersham). The purification method was carried out in accordance with the instructions attached to the GSTrapFF column.

2. Isolation of Gene Encoding Human 17βHSD Type 3 and Enzyme Purification

A full-length cDNA encoding human 17βHSD type 3 used in the pharmacological test of the present invention was obtained by the PCR method using a cDNA derived from human testis as a template. The nucleotide sequence of the obtained cDNA was analyzed by the dideoxyterminator method, and the clone matched with the known human 17βHSD type 3 sequence (GenBank accession No. BC034281) was selected. Subsequently, human fetus kidney-derived cell line, 293 cells, were transformed with a plasmid containing the cDNA, and the cells were collected 24 hours later. The collected cells were then disrupted in a phosphate buffer solution containing 5% glycerol (500 μL per 100 mm-dish of a phosphate buffer solution (pH 7.4, 200 mM) containing 5% glycerol) and centrifuged (16000 rpm, 5 min, 4° C.), and the supernatant was used as an enzyme source.

3. Measurement of Enzyme Activities of Human 17βHSD Type 5 and Type 3

Enzyme activity was measured referring to Trevor M. Penning, et al., Biochem. J., 351, 67-77, (2000). Specifically, using a 100 mM potassium phosphate buffer (pH 6.0), (1) the enzyme purified in section 1 above at a final concentration of 10 μg/mL, (2) androstenedione at a final concentration of 300 nM, (3) NADPH at a final concentration of 200 μM, and (4) a test substance, were mixed to react at room temperature for 2 hours, and then the amount of testosterone produced was measured using DELFIA (registered trademark) Testosterone Reagents R050-201 (manufactured by PerkinElmer). The measurement was performed in accordance with the attached instructions. The amount of reduction of testosterone production in the presence of the compound was obtained as a relative value with respect to the amount of testosterone in the absence of the enzyme set at 0% and the amount of testosterone produced in the absence of the compound set at 100%. Then, $IC_{50}$ values were calculated by the Logistic regression method.

Further, as an in vitro model close to a living body, the above enzyme activity can be measured by using a cell which expresses human 17βHSD type 5 or the like.

Further, LNCaP cells expressing human 17βHSD type 5 were constructed from a human prostate cancer-derived cell line, LNCaP cells, and a cell growth inhibitory activity of the compound of the present invention was evaluated.

4. Construction of LNCaP Cells Expressing Human 17βHSD Type 5

LNCaP cells of the human prostate cancer-derived cell line were transformed with a plasmid containing the clone selected in section 1 above and then a cell line showing stable expression was obtained.

5. Measurement of Cell Growth Capability Using LNCaP Cells Expressing Human 17βHSD type 5

9000 cells/well of the transformed cells obtained in section 4 above were seeded in a 96-well plate and cultured overnight. Then, androstenedione, in conjunction with a test compound, was added thereto at a final concentration of 10 nM, followed by culturing for 7 days. After the culturing, number of the cells was counted using a CellTiter-Glo (registered trademark) Luminescent Cell Viability Assay (Promega). The CellTiter-Glo (registered trademark) Luminescent Cell Viability Assay is a reagent that measures the number of the cells by monitoring an intracellular ATP level from the luminescence intensity by luciferase. The experimental manipulation was carried out in accordance with the attached instructions. The cell growth inhibitory activity in the presence of a test compound was calculated as a relative value with respect to the number of the cells in the absence of androstenedione set at proliferation of 0%, and the number of the cells in the presence of androstenedione and in the absence of the test compound set at proliferation of 100%. Then, $IC_{50}$ values were calculated by the Logistic regression method.

Table 1 shows the $IC_{50}$ values of inhibitory activity against human 17βHSD type 5 and type 3 of the Example compounds included in the compounds of the present invention, and the $IC_{50}$ values of cell growth inhibitory activity using human 17βHSD type 5-expressing LNCaP cells. Abbreviation "Ex" represents Example number.

TABLE 1

| Ex | Type 5 IC$_{50}$ (nM) | Type 3 IC$_{50}$ (nM) | LNCaP-17β5 IC$_{50}$ (nM) |
| --- | --- | --- | --- |
| 1 | 4.5 | >10,000 | 8.9 |
| 9 | 130 | >10,000 | 10 |
| 15 | 15 | >10,000 | 18 |
| 17 | 390 | >10,000 | 20 |
| 20 | 15 | >10,000 | 29 |
| 22 | 21 | >10,000 | 60 |
| 24 | 150 | >10,000 | 24 |
| 25 | 230 | >10,000 | 12 |
| 30 | 26 | >10,000 | 31 |

As shown by the test results above, the compounds of formula (I) hardly have an inhibitory activity against human 17βHSD type 3 and have an inhibitory activity selective to human 17βHSD type 5.

Accordingly, the compound of formula (I) can be used as an agent for preventing and/or treating a disease associated with 17βHSD type 5. For example, it can be used as an agent for preventing and/or treating a disease associated with androgen, since the androgen synthesis is suppressed by the inhibition of 17βHSD type 5.

Examples of diseases associated with androgen include prostate cancer, benign prostatic hyperplasia, acne, seborrhea, hirsutism, baldness, alopecia, precocious puberty, adrenal hypertrophy, polycystic ovary syndrome, breast cancer, endometriosis, leiomyoma, or the like. Examples thereof also include oxidative stress-associated diseases such as lung cancer.

Further, since 17βHSD type 5 is considered to be responsible for the intracrine androgen synthesis in the prostate, selective inhibitors of 17βHSD type 5 are expected to suppress the intracrine androgen synthesis in the prostate selectively. Therefore, the compound of formula (I) can be used as an agent for preventing and/or treating a disease associated with androgen particularly in the prostate, namely prostate cancer and benign prostatic hyperplasia.

Further, as shown by the test results above, since the compounds of formula (I) have a very weak inhibitory activity against human 17βHSD type 3, they are expected to suppress the intracrine testosterone synthesis selectively in the prostate by their selective inhibitory effects against 17βHSD type 5 without affecting biosynthesis of testosterone derived from human 17βHSD type 3 in the testes. In other words, since the compounds of formula (I) do not influence the concentration of testosterone in the blood, it can be used as an agent for treating and/or preventing benign prostatic hyperplasia and prostate cancer without adverse effects such as sexual dysfunction due to lowering of the blood testosterone concentration, and the like.

Further, as shown by the test results above, since the compounds of formula (I) exhibit a cell growth inhibitory activity in the human 17βHSD type 5-expressing LNCaP cells, they suppress intracrine testosterone synthesis selectively in prostate cancer by their selective inhibitory effects against 17βHSD type 5, thus can be used for treating and/or preventing prostate cancer without adverse effects.

Further, a commercial package is also useful which contains the above-mentioned pharmaceutical composition and a description including the above-mentioned effects.

A preparation containing one or two or more kinds of the compound of formula (I) or a salt thereof as an active ingredient can be prepared in accordance with a generally used method, using a pharmaceutical carrier, excipient, or the like, that is usually used in the art.

The administration can be carried out in any form of oral administration via tablets, pills, capsules, granules, powders, liquid preparations, or the like, or parenteral administration via injections such as intraarticular injection, intravenous injection, intramuscular injection, or the like, as well as suppositories, eye drops, eye ointments, percutaneous liquid preparations, ointments, percutaneous patches, transmucosal liquid preparations, transmucosal patches, inhalations, and the like.

As solid compositions for oral administration according to the present invention, tablets, powders, granules, or the like are used. In such a solid composition, one or two or more kinds of active ingredients are mixed with at least one inert excipient such as lactose, mannitol, glucose, hydroxypropylcellulose, microcrystalline cellulose, starch, polyvinyl pyrrolidone, and/or magnesium aluminometasilicate. According to a conventional method, the composition may contain inert additives such as a lubricant such as magnesium stearate, a disintegrator such as sodium carboxymethyl starch, a stabilizing agent, and a solubilizing agent. As occasion demands, the tablets or the pills may be coated with a sugar coating, or a film of gastric or enteric materials.

Liquid compositions for oral administration include pharmaceutically acceptable emulsions, solutions, suspensions, syrups, elixirs, or the like, and contain a generally used inert diluent such as purified water or ethanol. In addition to the inert diluent, the liquid composition may contain an adjuvant such as a solubilizing agent, a moistening agent, and a suspending agent, a sweetener, a flavor, an aroma, and an antiseptic.

Injections for parenteral administration include sterile aqueous or non-aqueous solutions, suspensions or emulsions. The aqueous solvent includes, for example, distilled water for injection or physiological saline. Examples of the non-aqueous solvent include propylene glycol, polyethylene glycol, vegetable oils such as olive oil, alcohols such as ethanol, Polysorbate 80 (Japanese Pharmacopeia), and the like. Such a composition may further contain a tonicity agent, an antiseptic, a moistening agent, an emulsifying agent, a dispersing agent, a stabilizing agent, or a solubilizing agent. These are sterilized, for example, by filtration through a bacteria-retaining filter, blending of a sterilizing agent, or irradiation. In addition, these can also be used by preparing a sterile solid composition, and dissolving or suspending it in sterile water or a sterile solvent for injection prior to use.

External preparations include ointments, plasters, creams, jellies, cataplasms, sprays, lotions, eye drops, eye ointments, and the like. Generally used ointment bases, lotion bases, aqueous or non-aqueous liquids, suspensions, emulsions, and the like are included. Examples of the ointment or lotion bases include polyethylene glycol, propylene glycol, white Vaseline, bleached beeswax, polyoxyethylene hydrogenated castor oil, glyceryl monostearate, stearyl alcohol, cetyl alcohol, lauromacrogol, sorbitan sesquioleate, and the like.

As the transmucosal preparations such as inhalations and transnasal preparations, a solid, liquid or semi-solid form are used, and can be prepared in accordance with a conventionally known method. For example, a known excipient, and also a pH-adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device. The dry powder inhalation devices or the like may be for single or multiple administration use, and a dry powder or a powder-containing capsule can be used. Alternatively, it may be in a form such as a pressurized aerosol spray or the like which uses an appropriate propellant, for example, a suitable gas such as chlorofluoroalkane, hydrofluoroalkane, or carbon dioxide and the like.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

The compounds of formula (I) can be used in combination with various agents for treating or preventing the diseases for which the aforementioned compounds of formula (I) are considered to be effective. The combined preparation may be administered simultaneously, or separately and continuously or at a desired time interval. The preparations to be co-administered may be a blend, or may be prepared individually.

EXAMPLES

The production processes for the compounds of formula (I) as an active ingredient of the present invention will be described below as Examples. In addition, production processes for novel compounds among the compounds used as starting materials of the compounds of formula (I) will be described as Production Examples. The production processes for the compounds of formula (I) are not limited to the production processes in specific Examples shown below and can be produced by a combination of these production processes or known production processes.

The following Examples are described to explain the present invention in more detail, and the present invention is not limited to the following Examples. Although the present invention is fully explained by way of the Examples, it should be understood that those skilled in the art will appreciate that various alterations and modifications can naturally be made. Accordingly, these alterations and modifications are included in the present invention unless they depart from the scope of the present invention.

The following abbreviations are used in Production Examples, Examples and Tables below.

Ex: Example number, REx: Production Example number, No: compound number, mp: melting point, Data: physicochemical data (FAB+: FAB-MS (M+H)$^+$, FAB−: FAB-MS (M−H)$^−$, ESI+: ESI-MS (M+H)$^+$, ESI−: ESI-MS (M−H)$^−$, API+: API-ES-MS (M+H)$^+$, EI: EI-MS (M)$^+$, CI: CI-MS (M+H)$^+$, NMR-DMSO-d6: δ(ppm) of peak(s) in $^1$H NMR in DMSO-d$_6$), Str: Structural formula, Syn (REx): Production Example numbers in which the corresponding compounds were produced using the same method, Syn (Ex): Example numbers in which the corresponding compounds were produced using the same method, DME: dimethoxyethane, DMF: N,N-dimethylformamide, DMSO: dimethyl sulfoxide, THF: tetrahydrofuran, 4M HCl/EtOAc: 4 mol/L hydrochloric acid-ethyl acetate solution, MeCN: acetonitrile, MeOH: methanol, tBuOH: tert-butyl alcohol, RT: retention time (minutes) in HPLC.

Production Example 1

3 g of sodium bicarbonate was added to a solution of 5 g of ethyl piperidin-4-yl acetate in 50 mL of dioxane and 50 mL of water at 0° C., and 4.6 mL of benzyl chloroformate was added thereto dropwise, followed by stirring at room temperature for 3 days. The reaction liquid was concentrated to half volume under reduced pressure, followed by extraction with ethyl acetate. The organic layer was washed with water and a saturated aqueous sodium chloride solution, dried over anhydrous sodium sulfate, and then concentrated under reduced pressure to obtain 8.9 g of benzyl 4-(2-ethoxy-2-oxoethyl)piperidine-1-carboxylate as a colorless oily substance.

Production Example 2

To a solution of 8.9 g of benzyl 4-(2-ethoxy-2-oxoethyp-piperidine-1-carboxylate in 100 mL of THF was added at 0° C. 46 mL of 1.4M methyl magnesium bromide of toluene-THF, followed by stirring at room temperature for 3 hours. 1M aqueous ammonium chloride solution was added to the reaction liquid, followed by extraction with ethyl acetate. The aqueous layer was extracted with ethyl acetate. The combined organic layers were washed with saturated aqueous sodium chloride solution, dried over anhydrous sodium sulfate, and then concentrated under reduced pressure to obtain 8.5 g of benzyl 4-(2-hydroxy-2-methylpropyl)piperidine-1-carboxylate as a colorless oily substance.

Production Example 3

To a solution of 8.5 g of benzyl 4-(2-hydroxy-2-methylpropyl)piperidine-1-carboxylate in 120 mL of methanol was added 500 mg of 10% palladium-carbon, followed by stirring under a hydrogen atmosphere at room temperature for 1 day. Insoluble material was removed by filtration through Celite, and the filtrate was concentrated under reduced pressure to obtain 5.6 g of 2-methyl-1-(piperidin-4-yl)-2-propanol as a white solid.

Production Example 4

To a solution of 250 mg of ethyl 7-chloro-5-fluoro-1H-indole-2-carboxylate in 2 mL of methanol was added 5 mL of 1M aqueous sodium hydroxide solution, followed by stirring at room temperature for 3 hours. The reaction liquid was adjusted to an acidic condition by adding a 1M aqueous hydrochloric acid solution, followed by extraction with ethyl acetate. The organic layer was washed with saturated brine, dried over anhydrous sodium sulfate and then concentrated under reduced pressure to obtain 210 mg of 7-chloro-5-fluoro-1H-indole-2-carboxylic acid as a white solid.

Production Example 5

To a solution of 250 mg of tert-butyl 4-(2-oxoethyl)piperidine-1-carboxylate in 5 mL of THF was added 1.2 mL of 1.4M methyl magnesium bromide in toluene-THF, followed by stirring at room temperature for 2 hours. Water was added to the reaction liquid, followed by extraction with ethyl acetate. The organic layer was washed with saturated brine, dried over anhydrous sodium sulfate, and then concentrated under reduced pressure. The residue was purified by silica gel column chromatography [chloroform:methanol=1:0-10:1] to obtain 236 mg of tert-butyl 4-(2-hydroxypropyl)piperidine-1-carboxylate as a colorless oily substance.

TABLE 2

| REx | Syn(REx) | Str | Data |
|---|---|---|---|
| 1 | 1 | benzyl 4-(2-methoxy-2-oxoethyl)piperidine-1-carboxylate | FAB+: 306 |
| 2 | 2 | benzyl 4-(2-hydroxy-2-methylpropyl)piperidine-1-carboxylate | CI+: 292 |
| 3 | 3 | 2-methyl-1-(piperidin-4-yl)propan-2-ol | EI: 157 |
| 4 | 4 | 7-chloro-5-fluoro-1H-indole-2-carboxylic acid | FAB−: 212 |
| 5 | 5 | tert-butyl 4-(2-hydroxypropyl)piperidine-1-carboxylate | FAB+: 244 |

Example 1

To a solution of 370 mg of 5-chloroindole-2-carboxylic acid and 300 mg of 2-methyl-1-(piperidin-4-yl)-2-propanol in 8 mL of DMF were added 360 mg of 1-ethyl-3-(dimethylaminopropyl)carbodiimide hydrochloride and 250 mg of 1-hydroxybenzotriazole, followed by stirring at room temperature for 1 day. 0.5M aqueous hydrochloric acid was added to the reaction liquid, followed by extraction with ethyl acetate. The organic layer was washed with 0.5 M aqueous sodium hydroxide solution and saturated aqueous sodium chloride solution, dried over anhydrous sodium sulfate, and then concentrated under reduced pressure. The residue was purified by silica gel column chromatography [chloroform:methanol=1:0-10:1], and then crystallized from diisopropyl ether to obtain 268 mg of 1-{1-[(5-chloro-1H-indol-2-yl)carbonyl]piperidin-4-yl}-2-methylpropan-2-ol as a white crystal.

Example 24

To a solution of 1800 mg of 5-methylindole-2-carboxylic acid and 1500 mg of 2-methyl-1-(piperidin-4-yl)-2-propanol in 25 mL of DMF were added 2100 mg of 1-ethyl-3-(dimethylaminopropyl)carbodiimide hydrochloride and 1500 mg of 1-hydroxybenzotriazole, followed by stirring at room temperature for 1 day. 0.5M aqueous hydrochloric acid was added to the reaction liquid, followed by extraction with ethyl acetate. The organic layer was washed with 0.5M aqueous sodium hydroxide solution and saturated aqueous sodium chloride solution, dried over anhydrous sodium sulfate, and then concentrated under reduced pressure. The residue was purified by silica gel column chromatography [chloroform:methanol=1:0-10:1], and then crystallized from a mixture of ethyl acetate/diisopropyl ether to obtain 2140 mg of 2-methyl-1-{1-[(5-methyl-1H-indol-2-yl)carbonyl]piperidin-4-yl}propan-2-ol as a white crystal.

Example 25

To a solution of 478 mg of 5-methoxyindole-2-carboxylic acid and 432 mg of 2-methyl-1-(piperidin-4-yl)-2-propanol in 8 mL of DMF were added 575 mg of 1-ethyl-3-(dimethylaminopropyl)carbodiimide hydrochloride and 169 mg of 1-hydroxybenzotriazole, followed by stirring at room temperature for 1 day. 0.2M aqueous hydrochloric acid was added to the reaction liquid, followed by extraction with ethyl acetate. The organic layer was washed with 0.2M aqueous sodium hydroxide solution and saturated aqueous sodium chloride solution, dried over anhydrous sodium sulfate, and then concentrated under reduced pressure. The residue was purified by silica gel column chromatography [chloroform:methanol=1:0-24:1], and then crystallized from a mixture of ethyl acetate/diisopropyl ether to obtain 683 mg of 1-{1-[(5-methoxy-1H-indol-2-yl)carbonyl]piperidin-4-yl}-2-methylpropan-2-ol as a white crystal.

Example 26

To a solution of 150 mg of 5H-[1,3]dioxolo[4,5-f]indole-6-carboxylic acid in 3 mL of dichloromethane was added 1.5 mL of a 1M boro tribromide dichloromethane solution at 0° C., followed by stirring at room temperature for 8 hours. Water was added to the reaction liquid, followed by extraction with ethyl acetate. The aqueous layer was extracted with ethyl acetate. The combined organic layers were washed with saturated aqueous sodium chloride solution, dried over anhydrous sodium sulfate, and then concentrated under reduced pressure. To a solution of the resulting white solid in 3 mL of DMF were added 140 mg of 2-methyl-1-(piperidin-4-yl)-2-propanol, 150 mg of 1-ethyl-3-(dimethylaminopropyl)carbodiimide hydrochloride and 105 mg of 1-hydroxybenzotriazole, followed by stirring at room temperature for 1 day. 0.5M aqueous hydrochloric acid was added to the reaction liquid, followed by extraction with ethyl acetate. The organic layer was washed with 0.5M aqueous sodium hydroxide solution and saturated aqueous sodium chloride solution, dried over anhydrous sodium sulfate, and then concentrated under reduced pressure. The residue was purified by silica gel column chromatography [chloroform:methanol=1:0-10:1], and then solidified using ethyl acetate-hexane to obtain 42 mg of 2-{[4-(2-hydroxy-2-methylpropyl)piperidin-1-yl]carbonyl}-1H-indole-5,6-diol as a white solid.

Example 27

To a solution of 838 mg of 2-methyl-1-{1-[(5-nitro-1H-indol-2-yl)carbonyl]piperidin-4-yl}propan-2-ol in 15 mL of methanol was added 80 mg of 10% palladium-carbon, followed by stirring under a hydrogen atmosphere at room temperature for 1 day. Insoluble material was removed by filtration through Celite, and the filtrate was concentrated under reduced pressure. The residue was purified by silica gel column chromatography [chloroform:methanol=1:0-10:1], and then solidified from hexane-ethyl acetate to obtain 576 mg of 1-{1-[(5-amino-1H-indol-2-yl)carbonyl]piperidin-4-yl}-2-methylpropan-2-ol as a pale brown solid.

Example 28

To a solution of 105 mg of 1-{1-[(5-amino-1H-indol-2-yl)carbonyl]piperidin-4-yl}-2-methylpropan-2-ol in 2 mL of dioxane and 2 mL of THF was added 32 μL of acetic anhydride, followed by stirring at room temperature for 2 hours. Water was added to the reaction liquid, followed by extraction with ethyl acetate. The organic layer was washed with saturated aqueous sodium chloride solution, dried over sodium sulfate, and then concentrated under reduced pressure. The residue was purified by silica gel column chromatography [chloroform:methanol=1:0-10:1], and then solidified using ethyl acetate-hexane to obtain 110 mg of N-(2-{[4-(2-hydroxy-2-methylpropyl)piperidin-1-yl]carbonyl}-1H-indol-5-yl) acetamide as a white solid.

Example 29

To a solution of 127 mg of 1-{1-[(5-amino-1H-indol-2-yl)carbonyl]piperidin-4-yl}-2-methylpropan-2-ol in 3 mL of methanol were added 90 μl, of 2,5-dimethoxytetrahydrofuran and 1 mL of acetic acid, followed by stirring at 60° C. for 1 day. 1M hydrochloric acid was added to the reaction liquid which was then extracted with ethyl acetate. The organic layer was washed with saturated aqueous sodium chloride solution, dried over anhydrous sodium sulfate, and then concentrated under reduced pressure. The residue was purified by silica gel column chromatography [chloroform:methanol=1:0-10:1], and then solidified from ethyl acetate-hexane to obtain 30 mg of 2-methyl-1-(1-{[5-(1H-pyrrol-1-yl)-1H-indol-2-yl]carbonyl}piperidin-4-yl)propan-2-ol as a white solid.

Example 30

To a solution of 233 mg of tert-butyl 4-(2-hydroxy propyl)piperidine-1-carboxylate in 4 mL of ethyl acetate was added 3 mL of 4M HCl/EtOAc, followed by stirring at room temperature for 2 hours. The reaction liquid was concentrated under reduced pressure to obtain 4-(2-hydroxypropyl)piperidine hydrochloride. To a solution of the 4-(2-hydroxypropyl)piperidine hydrochloride and 155 mg of indole-2-carboxylic acid in 5 mL of DMF were added 0.15 mL of triethylamine, 190 mg of 1-ethyl-3-(dimethylaminopropyl)carbodiimide hydrochloride and 130 mg of 1-hydroxybenzotriazole, followed by stirring at room temperature for 1 day. 0.5M aqueous hydrochloric acid was added to the reaction liquid, followed by extraction with ethyl acetate. The organic layer was washed with 0.5M aqueous sodium hydroxide solution and saturated brine, dried over anhydrous sodium sulfate, and then concentrated under reduced pressure. The residue was purified by silica gel column chromatography [chloroform:methanol=1:0-10:1], and then solidified using diisopropyl ether to obtain 49 mg of 1-[1-(1H-indol-2-ylcarbonyl)piperidin-4-yl]propan-2-ol as a white solid.

Example 31

To a solution of 500 mg of indole-2-carboxylic acid and 530 mg of ethyl piperidin-3-yl acetate in 8 mL of DMF were added 610 mg of 1-ethyl-3-(dimethylaminopropyl)carbodiimide hydrochloride and 430 mg of 1-hydroxybenzotriazole, followed by stirring at room temperature for 2 hours. 0.5M aqueous hydrochloric acid was added to the reaction liquid, followed by extraction with ethyl acetate. The organic layer was washed with 0.5M aqueous sodium hydroxide solution and saturated aqueous sodium chloride solution, dried over anhydrous sodium sulfate, and then concentrated under reduced pressure to obtain 519 mg of ethyl[1-(1H-indol-2-ylcarbonyl)piperidin-3-yl]acetate. To a solution of 392 mg of the resulting ethyl[1-(1H-indol-2-ylcarbonyl)piperidin-3-yl]acetate in 7 mL of THF was added 30 mg of lithium borohydride, followed by stirring at room temperature for 1 day. Water was added to the reaction liquid, followed by extraction with ethyl acetate. The organic layer was washed with saturated aqueous sodium chloride solution, dried over anhydrous sodium sulfate, and then concentrated under reduced pressure. The resulting residue was purified by silica gel column chromatography [hexane:ethyl acetate=1:0-2:1], and then crystallized from diisopropyl ether to obtain 92 mg of 2-[1-(1H-indol-2-ylcarbonyl)piperidin-3-yl]ethanol as a white solid.

Example 32

To a solution of 4.1 mg of 4-piperidine ethanol, 5.3 mg of 5-fluoro-1H-indole-2-carboxylic acid, and 4.0 mg of 1-hydroxybenzotriazole in 0.6 mL of DMF was added 100 mg of PS-Carbodiimide (Argonaut Technologies) at room temperature, followed by stirring overnight. To the reaction liquid were added 50 mg of MP-Carbonate (Argonaut Technologies) and 50 mg of PS-Isocyanate (Argonaut Technologies) at room temperature, followed by stirring for 2 hours, and insoluble material was filtered. The filtrate was concentrated under reduced pressure to obtain 8.8 mg of 2-{1-[(5-fluoro-1H-indol-2-yl)carbonyl]piperidin-4-yl}ethanol.

The conditions of HPLC performed for the determination of RT are shown below.

Column: Wakosil-II 5C18AR (registered trademark) (particle size: 5 μm, inner diameter: 2.0 mm, and length: 30 mm)

TABLE 3

| Time (min) | A sol (%) | B sol (%) |
|---|---|---|
| 0-4 | 90→0 | 10→100 |
| 4-4.5 | 0 | 100 |

Mobile phase: A sol, 5 mM aqueous trifluoroacetic acid solution, and B sol, methanol Flow rate: 1.2 mL/min Detection wavelength: 254 nm Column temperature: 35.0° C.

Injection volume: 5 μL

The compounds of Examples up to Example 48 shown in the following Tables were produced in the same manner as in the above-mentioned Examples. Production processes and structures of respective Example compounds are shown in Tables 4, 5, 8 and 9, and the physicochemical data are shown in Tables 6, 7 and 10.

In addition, structures of other compounds of the present invention are shown in Table 11. These compounds can be easily produced according to the above-mentioned production processes, methods described in Examples, and methods apparent to those skilled in the art, or modified methods thereof.

TABLE 4

| Ex | Syn (Ex) | Str |
|---|---|---|
| 1 | 1 | 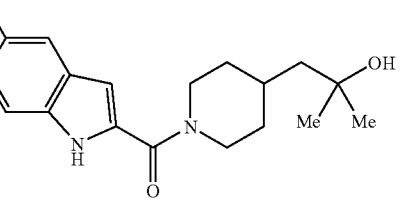 |
| 2 | 1 | 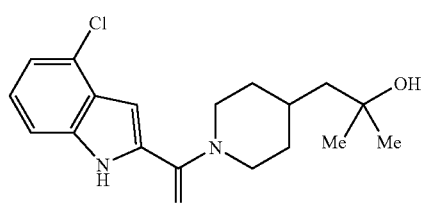 |
| 3 | 1 | 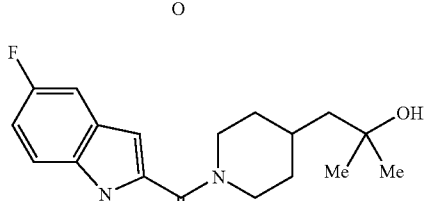 |

TABLE 4-continued

| Ex | Syn (Ex) | Str |
|---|---|---|
| 4 | 1 | 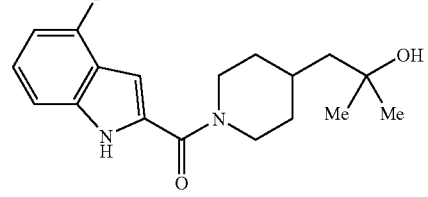 |
| 5 | 1 | 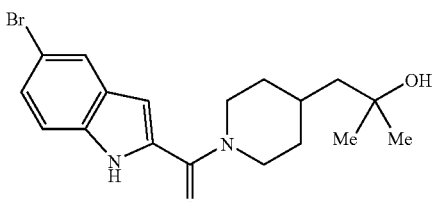 |
| 6 | 1 | 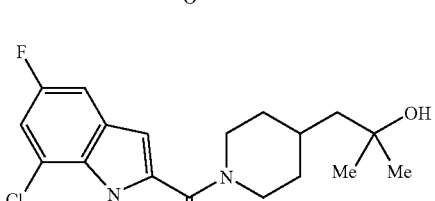 |
| 7 | 1 | 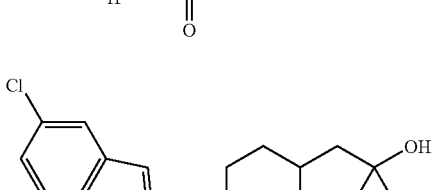 |
| 8 | 1 | 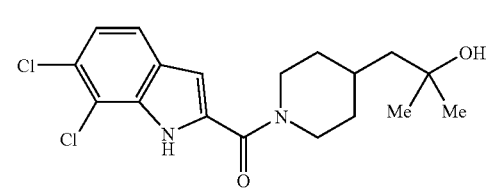 [SMILES: CC(C)(O)CC1CCN(C(=O)c2cc3ccc(Cl)c(Cl)c3[nH]2)CC1] |
| 9 | 1 | 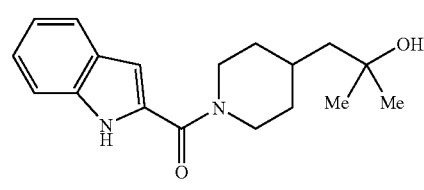 [SMILES: CC(C)(O)CC1CCN(C(=O)c2cc3ccccc3[nH]2)CC1] |
| 10 | 1 | 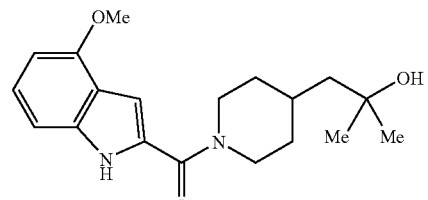 |

TABLE 4-continued

| Ex | Syn (Ex) | Str |
|---|---|---|
| 11 | 1 | 6-MeO-indole-2-carbonyl-piperidine-4-CH₂C(Me)₂OH |
| 12 | 1 | 5-F₃CO-indole-2-carbonyl-piperidine-4-CH₂C(Me)₂OH |
| 13 | 1 | 5-BnO-indole-2-carbonyl-piperidine-4-CH₂C(Me)₂OH |
| 14 | 1 | indole-2-carbonyl-piperidine-4-CH₂CH₂OMe |
| 15 | 1 | 5-HO-indole-2-carbonyl-piperidine-4-CH₂C(Me)₂OH |
| 16 | 1 | 5,6-methylenedioxy-indole-2-carbonyl-piperidine-4-CH₂C(Me)₂OH |

TABLE 5

| Ex | Syn (Ex) | Str |
|---|---|---|
| 17 | 1 | 4,3-diMe-indole-2-carbonyl-piperidine-4-CH₂C(Me)₂OH |
| 18 | 1 | 4-Me-indole-2-carbonyl-piperidine-4-CH₂C(Me)₂OH |
| 19 | 1 | 5-tBu-indole-2-carbonyl-piperidine-4-CH₂C(Me)₂OH |
| 20 | 1 | 5-O₂N-indole-2-carbonyl-piperidine-4-CH₂C(Me)₂OH |
| 21 | 1 | indole-2-carbonyl-piperidine-4-CH₂CH₂OH |
| 22 | 1 | 5-Me-indole-2-carbonyl-piperidine-4-CH₂CH₂OH |
| 23 | 1 | indole-2-carbonyl-piperidine-2-CH₂CH₂OH |
| 24 | 24 | 5-Me-indole-2-carbonyl-piperidine-4-CH₂C(Me)₂OH |

TABLE 5-continued

| Ex | Syn (Ex) | Str |
|---|---|---|
| 25 | 25 | 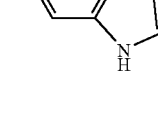 |
| 26 | 26 | 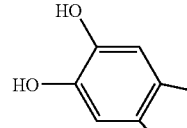 |
| 27 | 27 | 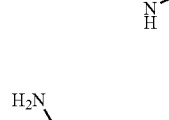 |
| 28 | 28 | 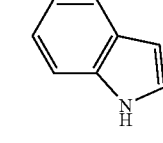 |
| 29 | 29 | 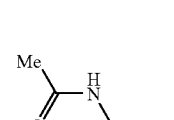 |
| 30 | 30 | 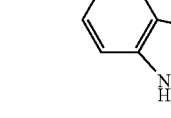 |
| 31 | 31 | 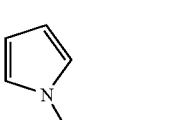 |

TABLE 6

| Ex | Data |
|---|---|
| 1 | NMR-DMSOd6 (400 MHz): 1.09-1.21 (8H, m), 1.33 (2H, d, J = 5.6 Hz), 1.75-1.89 (3H, m), 3.03 (2H, m), 4.12 (1H, s), 4.34 (2H, m), 6.71 (1H, m), 7.17 (1H, m), 7.41 (1H, m), 7.65 (1H, m), 11.74 (1H, s); FAB+: 335; mp: 178-180° C. |
| 2 | FAB+: 335 |
| 3 | FAB+: 319 |
| 4 | FAB+: 319 |
| 5 | FAB+: 379 |
| 6 | FAB+: 353 |
| 7 | FAB+: 369 |
| 8 | FAB+: 369 |
| 9 | NMR-DMSOd6 (400 MHz): 1.11-1.21 (8H, m), 1.34 (2H, d, J = 5.6 Hz), 1.76-1.88 (3H, m), 3.03 (2H, m), 4.12 (1H, s), 4.37 (2H, m), 6.72 (1H, m), 7.03 (1H, m), 7.17 (1H, m), 7.40 (1H, m), 7.59 (1H, m), 11.51 (1H, s); FAB+: 301; mp: 153-163° C. |
| 10 | FAB+: 331 |
| 11 | FAB+: 331 |
| 12 | FAB+: 385 |
| 13 | FAB+: 407 |
| 14 | FAB+: 287 |
| 15 | NMR-DMSOd6 (400 MHz): 1.08-1.21 (8H, m), 1.33 (2H, d, J = 5.2 Hz), 1.72-1.87 (3H, m), 2.82-3.17 (2H, m), 4.11 (1H, s), 4.36 (2H, d, J = 13.2 Hz), 6.53 (1H, m), 6.70 (1H, m), 6.87 (1H, m), 7.20 (1H, m), 8.76 (1H, s), 11.20 (1H, s); FAB+: 317; mp: 212-219° C. |
| 16 | FAB+: 345 |
| 17 | NMR-DMSOd6 (400 MHz): 1.05-1.18 (8H, m), 1.33 (2H, d, J = 5.2 Hz), 1.71-1.84 (3H, m), 2.21 (3H, s), 2.38 (3H, s), 2.97 (2H, m), 4.04 (2H, m), 4.10 (1H, s), 6.97 (1H, m), 7.20 (1H, m), 7.30 (1H, m), 11.01 (1H, s); FAB+: 329; mp: 166-168° C. |
| 18 | FAB+: 315 |
| 19 | FAB+: 357 |
| 20 | NMR-DMSOd6 (400 MHz): 1.11-1.23 (8H, m), 1.33 (2H, d, J = 5.2 Hz), 1.77-1.90 (3H, m), 2.77-3.28 (2H, m), 4.12 (1H, s), 4.34 (2H, m), 7.03 (1H, m), 7.56 (1H, m), 8.07 (1H, m), 8.64 (1H, m), 12.28 (1H, s); FAB+: 346; mp: 223-225° C. |

TABLE 7

| Ex | Data |
|---|---|
| 21 | EI: 272 |
| 22 | NMR-DMSOd6 (400 MHz): 1.11-1.19 (2H, m), 1.38-1.43 (2H, m), 1.73-1.76 (3H, m), 2.36 (3H, s), 2.98 (2H, s), 3.45-3.49 (2H, m), 4.37-4.44 (3H, m), 6.63 (1H, m), 7.00 (1H, m), 7.29 (1H, m), 7.36 (1H, s), 11.38 (1H, s); EI: 286; mp: 163-165° C. |
| 23 | FAB+: 273 |
| 24 | NMR-DMSOd6 (400 MHz): 1.08-1.21 (8H, m), 1.33 (2H, d, J = 5.6 Hz), 1.75-1.88 (3H, m), 2.36 (3H, s), 3.01 (2H, m), 4.11 (1H, s), 4.37 (2H, m), 6.62 (1H, m), 6.99 (1H, m), 7.29 (1H, m), 7.36 (1H, m), 11.37 (1H, s); FAB+: 315; mp: 149-150° C. |
| 25 | NMR-DMSOd6: 1.11-1.21 (8H, m), 1.33 (2H, d, J = 5.2 Hz), 1.75-1.88 (3H, m), 3.01 (2H, m), 3.75 (3H, s), 4.11 (1H, s), 4.36 (2H, m), 6.63 (1H, m), 6.82 (1H, m), 7.06 (1H, m), 7.29 (1H, m), 11.36 (1H, s); FAB+: 331; mp: 149-151° C. |
| 26 | FAB+: 333 |
| 27 | FAB+: 316 |
| 28 | FAB+: 358 |
| 29 | FAB+: 366 |
| 30 | NMR-DMSOd6 (400 MHz): 1.02-1.24 (6H, m), 1.34 (1H, m), 1.69-1.83 (3H, m), 2.81-3.18 (2H, m), 3.72 (1H, m), 4.36 (1H, d, J = 4.8 Hz), 4.42 (2H, m), 6.73 (1H, m), 7.03 (1H, m), 7.17 (1H, m), 7.40 (1H, m), 7.59 (1H, m), 11.52 (1H, s); FAB+: 287; mp: 163-167° C. |
| 31 | FAB+: 273 |

TABLE 8

| Ex | Syn (Ex) | Str |
|---|---|---|
| 32 | 32 | 5-fluoro-1H-indole-2-carbonyl-[4-(2-hydroxyethyl)piperidin-1-yl] |
| 33 | 32 | 5-chloro-1H-indole-2-carbonyl-[4-(2-hydroxyethyl)piperidin-1-yl] |
| 34 | 32 | 5-methoxy-1H-indole-2-carbonyl-[4-(2-hydroxyethyl)piperidin-1-yl] |
| 35 | 32 | 5-benzyloxy-1H-indole-2-carbonyl-[4-(2-hydroxyethyl)piperidin-1-yl] |
| 36 | 32 | 5-hydroxy-1H-indole-2-carbonyl-[4-(2-hydroxyethyl)piperidin-1-yl] |
| 37 | 32 | 5-methyl-1H-indole-2-carbonyl-[4-(2-hydroxyethyl)piperidin-1-yl] |
| 38 | 32 | 5-nitro-1H-indole-2-carbonyl-[4-(2-hydroxyethyl)piperidin-1-yl] |
| 39 | 32 | 6-fluoro-1H-indole-2-carbonyl-[4-(2-hydroxyethyl)piperidin-1-yl] |

TABLE 8-continued
| Ex | Syn (Ex) | Str |
|---|---|---|
| 40 | 32 | 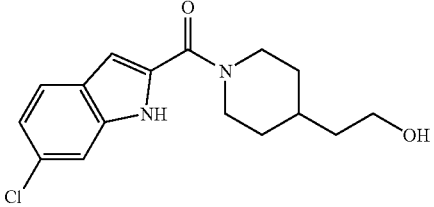 [SMILES: O=C(c1cc2ccc(Cl)cc2[nH]1)N1CCC(CCO)CC1] |
| 41 | 32 | 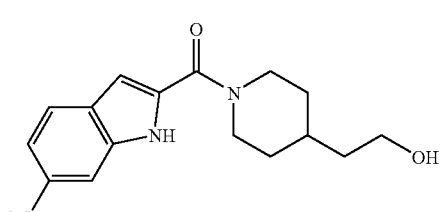 |
TABLE 9
| Ex | Syn (Ex) | Str |
|---|---|---|
| 42 | 32 | 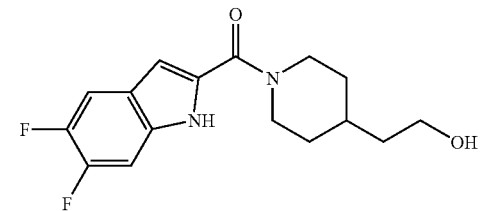 [SMILES: O=C(c1cc2cc(F)c(F)cc2[nH]1)N1CCC(CCO)CC1] |
| 43 | 32 | 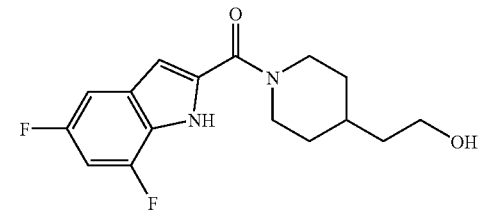 [SMILES: O=C(c1cc2cc(F)cc(F)c2[nH]1)N1CCC(CCO)CC1] |
| 44 | 32 | 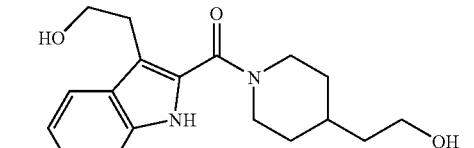 |
| 45 | 32 | 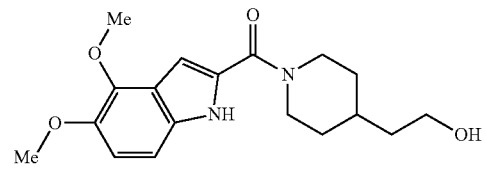 [SMILES: COc1ccc2[nH]c(C(=O)N3CCC(CCO)CC3)cc2c1OC] |
| 46 | 32 | 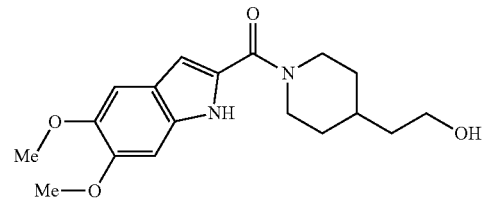 [SMILES: COc1cc2cc(C(=O)N3CCC(CCO)CC3)[nH]c2cc1OC] |
| 47 | 32 | 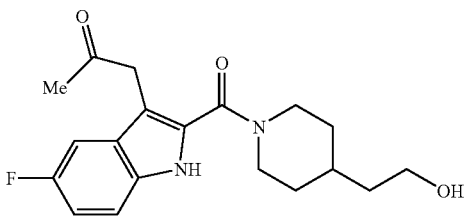 [SMILES: CC(=O)Cc1c(C(=O)N2CCC(CCO)CC2)[nH]c2ccc(F)cc12] |
| 48 | 32 | 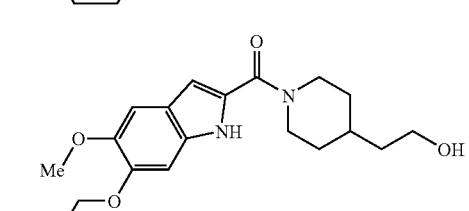 |
TABLE 10
| Ex | Data |
|---|---|
| 32 | RT: 2.16 ESI+: 291 |
| 33 | RT: 2.47 ESI+: 307 |
| 34 | RT: 1.94 ESI+: 303 |
| 35 | RT: 2.73 ESI+: 379 |
| 36 | RT: 1.21 ESI+: 289 |
| 37 | RT: 2.56 ESI+: 301 |
| 38 | RT: 2.01 ESI+: 318 |
| 39 | RT: 2.18 ESI+: 291 |
| 40 | RT: 2.45 ESI+: 307 |
| 41 | RT: 2.06 ESI+: 303 |
| 42 | RT: 2.29 ESI+: 309 |
| 43 | RT: 2.27 ESI+: 309 |
| 44 | RT: 1.69 ESI+: 317 |
| 45 | RT: 1.80 ESI+: 333 |
| 46 | RT: 1.74 ESI+: 333 |
| 47 | RT: 1.30 ESI+: 348 |
| 48 | RT: 2.48 ESI+: 409 |

TABLE 10-continued
| Ex | Data |
|---|---|
TABLE 11
| No | Str |
|---|---|
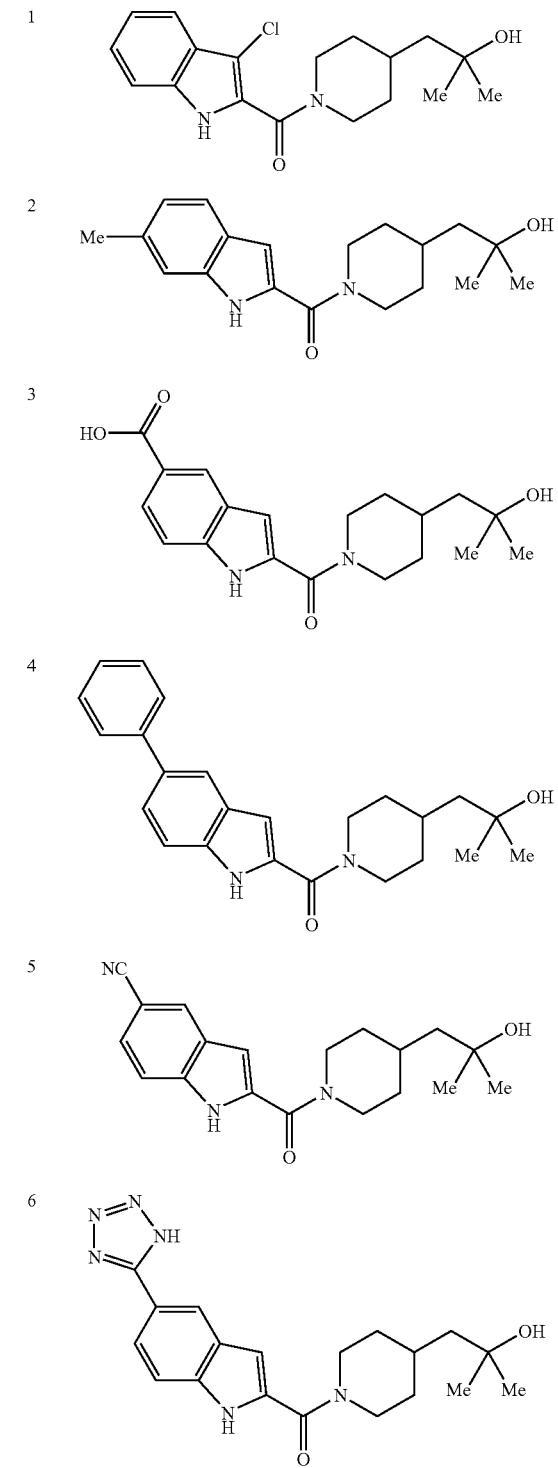
TABLE 11-continued
| No | Str |
|---|---|
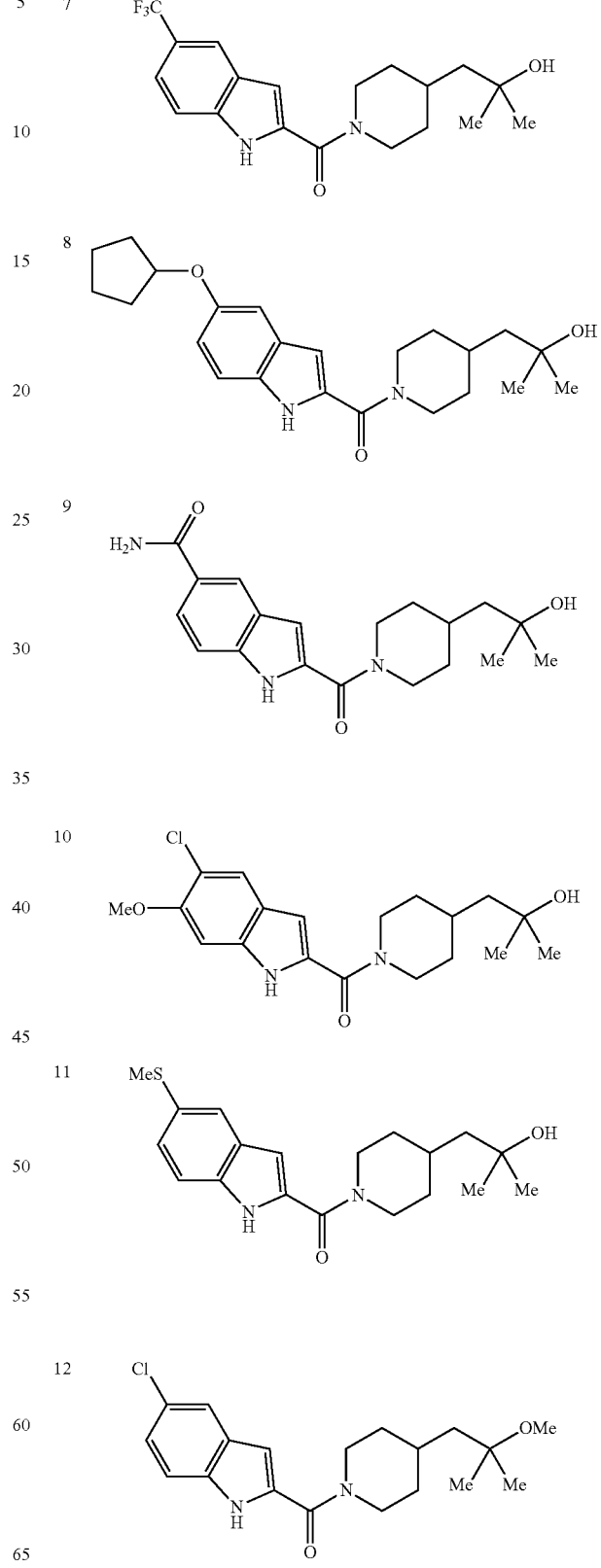

TABLE 11-continued

| No | Str |
|---|---|
| 13 | 5-(methylsulfonyl)-indole-2-carbonyl-[4-(2-hydroxy-2-methylpropyl)piperidine] |
| 14 | 5-chloro-indole-2-carbonyl-[4-(2-hydroxy-2-methylpropyl)piperidine] |
| 15 | 7-methyl-indole-2-carbonyl-[4-(2-hydroxy-2-methylpropyl)piperidine] |

INDUSTRIAL APPLICABILITY

Since the compound which is an active ingredient of the medicament of the present invention has a selective inhibitory effect against 17βHSD type 5 and an excellent pharmacological effect based thereon, the pharmaceutical composition of the present invention can be used as an agent for treating and/or preventing diseases associated with 17βHSD type 5, particularly prostate cancer, benign prostatic hyperplasia, acne, seborrhea, hirsutism, baldness, alopecia, precocious puberty, adrenal hypertrophy, polycystic ovary syndrome, breast cancer, lung cancer, endometriosis, leiomyoma, or the like.

The invention claimed is:

1. A compound according to formula (Ia) or a salt thereof:

[Structure (Ia): indole with R5, R6, R4, R7, R8 substituents, attached via 2-carbonyl to piperidine bearing CH2-C(R1)(R2)-OR3]

wherein
R$^1$, R$^2$, and R$^3$, which are the same or different from each other, are H or lower alkyl;
R$^4$ is H, lower alkyl, halogen, -loweralkylene-OR$^0$, or loweralkylene-CO-loweralkyl;
R$^5$ is H, lower alkyl, halogen, or —OR$^0$;
R$^6$ is H, lower alkyl, halogen, halogeno lower alkyl, —COOR$^0$, aryl, heterocyclic group, nitro, CN, —CONR$^{10}$R$^{11}$, NR$^{10}$R$^{11}$, —NR$^0$C(O)R$^{10}$, —OR$^0$, —O— halogeno lower alkyl, —SR$^0$, —S(O)$_2$-lower alkyl, —O-cycloalkyl, or —O-loweralkylene-aryl;
R$^7$ is H, lower alkyl, halogen, —O-loweralkylene-aryl, or —O-lower alkyl; or
R$^6$ and R$^7$ are combined to form —O-lower alkylene-O—;
R$^8$ is H, halogen, or lower alkyl;
R$^0$, which is the same or different from each other, is H or lower alkyl; and
R$^{10}$ and R$^{11}$, which are the same or different from each other, are H or lower alkyl.

2. The compound according to claim 1 or a salt thereof, wherein R$^1$ and R$^2$ are lower alkyl, and R$^3$ is H.

3. The compound according to claim 2 or a salt thereof, wherein R$^4$, R$^5$, R$^7$, and R$^8$, which are the same or different from each other, are H, lower alkyl, or halogen.

4. The compound according to claim 2 or a salt thereof, wherein R$^6$ is H, lower alkyl, halogen, halogeno lower alkyl, nitro, OH, or —O-lower alkyl.

5. The compound according to claim 4 or a salt thereof, wherein R$^6$ is lower alkyl, halogen, or —O-lower alkyl.

6. The compound according to claim 2, which is chosen from:
1-[1-(1H-indol-2-ylcarbonyl)piperidin-4-yl]-2-methylpropan-2-ol;
2-methyl-1-{1-[(4-methyl-1H-indol-2-yl)carbonyl]piperidin-4-yl}propan-2-ol;
2-methyl-1-{1-[(5-methyl-1H-indol-2-yl)carbonyl]piperidin-4-yl}propan-2-ol;
1-{1-[(3,5-dimethyl-1H-indol-2-yl)carbonyl]piperidin-4-yl}-2-methylpropan-2-ol;
1-{1-[(5-tert-butyl-1H-indol-2-yl)carbonyl]piperidin-4-yl}-2-methylpropan-2-ol;
1-{1-[(4-fluoro-1H-indol-2-yl)carbonyl]piperidin-4-yl}-2-methylpropan-2-ol;
1-{1-[(5-fluoro-1H-indol-2-yl)carbonyl]piperidin-4-yl}-2-methylpropan-2-ol;
1-{1-[(4-chloro-1H-indol-2-yl)carbonyl]piperidin-4-yl}-2-methylpropan-2-ol;
1-{1-[(5-chloro-1H-indol-2-yl)carbonyl]piperidin-4-yl}-2-methylpropan-2-ol;
1-{1-[(5-bromo-1H-indol-2-yl)carbonyl]piperidin-4-yl}-2-methylpropan-2-ol;
1-{1-[(7-chloro-5-fluoro-1H-indol-2-yl)carbonyl]piperidin-4-yl}-2-methylpropan-2-ol;
2-{[4-(2-hydroxy-2-methylpropyl)piperidin-1-yl]carbonyl}-1H-indol-5-ol;
1-{1-[(4-methoxy-1H-indol-2-yl)carbonyl]piperidin-4-yl}-2-methylpropan-2-ol;
1-{1-[(5-methoxy-1H-indol-2-yl)carbonyl]piperidin-4-yl}-2-methylpropan-2-ol;
1-{1-[(6-methoxy-1H-indol-2-yl)carbonyl]piperidin-4-yl}-2-methylpropan-2-ol;
2-methyl-1-(1-{[5-(trifluoromethoxy)-1H-indol-2-yl]carbonyl}piperidin-4-yl)propan-2-ol; and
2-methyl-1-{1-[(5-nitro-1H-indol-2-yl)carbonyl]piperidin-4-yl}propan-2-ol,
or a salt thereof.

7. The compound according to claim 6, which is 1-[1-(1H-indol-2-ylcarbonyl)piperidin-4-yl]-2-methylpropan-2-ol or a salt thereof.

8. The compound according to claim 6, which is 2-methyl-1-{1-[(5-methyl-1H-indol-2-yl)carbonyl]piperidin-4-yl}propan-2-ol or a salt thereof.

9. The compound according to claim 6, which is 1-{1-[(3,5-dimethyl-1H-indol-2-yl)carbonyl]piperidin-4-yl}-2-methylpropan-2-ol or a salt thereof.

10. The compound according to claim 6, which is 1-{1-[(5-chloro-1H-indol-2-yl)carbonyl]piperidin-4-yl}-2-methyl-propan-2-ol or a salt thereof.

11. The compound according to claim 6, which is 2-{[4-(2-hydroxy-2-methylpropyl)piperidin-1-yl]carbonyl}-1H-indol-5-ol or a salt thereof.

12. The compound according to claim 6, which is 1-{1-[(5-methoxy-1H-indol-2-yl)carbonyl]piperidin-4-yl}-2-methyl-propan-2-ol or a salt thereof.

13. The compound according to claim 6, which is 2-methyl-1-{1-[(5-nitro-1H-indol-2-yl)carbonyl]piperidin-4-yl}propan-2-ol or a salt thereof.

14. A pharmaceutical composition comprising the compound according to claim 1 or a salt thereof, and a pharmaceutically acceptable excipient.

* * * * *